United States Patent
Popovic et al.

(10) Patent No.: US 9,259,576 B2
(45) Date of Patent: Feb. 16, 2016

(54) FUNCTIONAL ELECTRICAL STIMULATION METHOD, USE AND APPARATUS FOR MOOD ALTERATION

(71) Applicant: UNIVERSITY HEALTH NETWORK, Toronto (CA)

(72) Inventors: Milos R. Popovic, Mississauga (CA); Jose Zariffa, Toronto (CA); Sander L. Hitzig, Toronto (CA)

(73) Assignee: UNIVERSITY HEALTH NETWORK, Toronto, Ontario (CA)

(*) Notice: Subject to any disclaimer, the term of this patent is extended or adjusted under 35 U.S.C. 154(b) by 0 days.

(21) Appl. No.: 14/204,829

(22) Filed: Mar. 11, 2014

(65) Prior Publication Data

US 2014/0277309 A1    Sep. 18, 2014

Related U.S. Application Data

(60) Provisional application No. 61/776,962, filed on Mar. 12, 2013.

(51) Int. Cl.
| | | |
|---|---|---|
| A61N 1/00 | (2006.01) | |
| A61N 1/36 | (2006.01) | |
| A61N 1/05 | (2006.01) | |
| A61N 1/04 | (2006.01) | |

(52) U.S. Cl.
CPC .......... *A61N 1/36096* (2013.01); *A61N 1/0452* (2013.01); *A61N 1/0504* (2013.01)

(58) Field of Classification Search
CPC .............. A61N 1/328; A61N 1/36025; A61N 1/36096; A61N 1/0452; A61N 1/0504
USPC ....................................... 607/1, 2, 66–75, 45
See application file for complete search history.

(56) References Cited

U.S. PATENT DOCUMENTS

| | | | |
|---|---|---|---|
| 7,844,340 B2* | 11/2010 | Pawlowicz, III | 607/46 |
| 2005/0038486 A1* | 2/2005 | Mulholland | 607/48 |
| 2010/0114240 A1* | 5/2010 | Guntinas-Lichius et al. | 607/48 |
| 2011/0218590 A1 | 9/2011 | DeGiorgio et al. | |

OTHER PUBLICATIONS

P. Ekman, R. J. Davidson and W. V. Friesen, "The Duchenne Smile: Emotional Expression and Brain Physiology. II," J. Pers. Soc. Psychol., vol. 58, pp. 342-353, Feb. 1990.

B. M. Waller, S. J. Vick, L. A. Parr, K. A. Bard, M. C. Pasqualini, K. M. Gothard and A. J. Fuglevand, "Intramuscular Electrical Stimulation of Facial Muscles in Humans and Chimpanzees: Duchenne Revisited and Extended," Emotion, vol. 6, No. 3, pp. 367-382, Aug. 2006.

W. E. Rinn, "The Neuropsychology of Facial Expression: A Review of the Neurological and Psychological Mechanisms for Producing Facial Expressions," Psychol. Bull., vol. 95, No. 1 pp. 52-77, Jan. 1984.

(Continued)

*Primary Examiner* — Scott Getzow
(74) *Attorney, Agent, or Firm* — Jason A. Bernstein; Barnes & Thornburg LLP

(57) ABSTRACT

A method and apparatus for providing functional electrical stimulation to an individual for altering a mood or emotional parameter associated with a mood or emotional state is provided. The method involves providing functional electrical stimulation to facial muscles of the individual so as to elicit a detectable contraction in said muscles associated with a facial expression associated with a desired mood or emotional parameter.

19 Claims, 6 Drawing Sheets

(56) References Cited

OTHER PUBLICATIONS

H. C. Hopf, W. Muller-Forell and N. J. Hopf, "Localization of emotional and volitional facial paresis," Neurology, vol. 42, pp. 1918-1923, Oct. 1992.

M. Iwase, Y. Ouchi, H. Okada, C. Yokoyama, S. Nobezawa, E. Yoshikawa, H. Tsukada, M. Takeda, K. Yamashita, M. Takeda, K. Yamaguti, H. Kuratsune, A. Shimizu and Y. Watanabe, "Neural Substrates of Human Facial Expression of Pleasant Emotion Induced by Comic Films: a PET Study," Neuroimage, vol. 17, pp. 758-768, Oct. 2002.

P. Ekman and R. J. Davidson, "Voluntary Smiling Changes Regional Brain Activity." Psch. Sci., vol. 4, No. 5, pp. 342-345, Sep. 1993.

D. Wiswede, T. F. Munte, U. M. Kramer and J. Russeler, "Embodied Emotion Modulates Neural Signature of Performance Monitoring," PLoS One, vol. 4, Issue 6, pp. 1-6 e5754, Jun. 2009.

M. B. Lewis, "Exploring the Positive and Negative Implications of Facial Feedback." Emotion, vol. 12, No. 4, pp. 852-859, 2012.

A. Hennenlotter, C. Dresel, F. Castrop, A. O. Ceballos-Baumann, A. M. Wohlschlager and B. Haslinger, "The Link between Facial Feedback and Neural Activity within Central Circuitries of Emotion—New Insights from Botulinum Toxin-Induced Denervation of fFown Muscles," Cereb. Cortex, vol. 19, pp. 537-542, Mar. 2009.

M. G. Frank and P. Ekman, "Physiologic Effects of the Smile." Directions in Psychiatry, vol. 16, Lesson 25, pp. 1-8, Dec. 1996.

R. Soussignan, "Duchenne Smile, Emotional Experience, and Autonomic Reactivity: A Test of the Facial Feedback Hypothesis," Emotion, vol. 2, No. 1, pp. 52-74, Mar. 2002.

M. R. Popovic, N. Kapadia, V. Zivanovic, J. C. Furlan, B. C. Craven and C. McGillivray, "Functional Electrical Stimulation Therapy of Voluntary Grasping Versus Only Conventional Rehabilitation for Patients with Subacute Incomplete Tetraplegia: A Randomized Clinical Trial," Neurorehabil. Neural Repair, vol. 25, pp. 433-442, Jun. 2011.

T. A. Thrasher, V. Zivanovic, W. McIlroy and M. R. Popovic, "Rehabilitation of Reaching and Grasping Function in Severe Hemiplegic Patients Using Functional Electrical Stimulation Therapy," Neurorehabil. Neural Repair, vol. 22, pp. 706-714, Nov.-Dec. 2008.

E. Beaumont, E. Guevara, S. Dubeau, F. Lesage, M. Nagai and M. R. Popovic, "Functional electrical stimulation post-spinal cord injury improves locomotion and increases afferent input into the central nervous system in rats" Journal of Spinal Cord Medicine, vol. 37, No. 1 pp. 93-100, 2014.

N. Kawashima, M. Popovic and V. Zivanovic, "Effect of Intensive Functional Electrical Stimulation Therapy on the Upper Limb Motor Recovery after Stroke: Case Study of a Patient with Chronic Stroke," Physiotherapy Canada, vol. 65 pp. 20-28, 2013.

D. McDonnall, K. S. Guillory and M. D. Gossman, "Restoration of blink in facial paralysis patients using FES," in Proceedings of the 4th International IEEE EMBS Conference on Neural Engineering, Antalya, Turkey, pp. 76-79 2009.

P. J. Ohtake, M. L. Zafron, L. G. Poranki and D. R. Fish, "Does electrical stimulation improve motor recovery in patients with idiopathic facial (Bell) palsy?" Phys. Ther., vol. 86, No. 11, pp. 1558-1564, Nov. 2006.

F. Schneider, R. C. Gur, R. E. Gur and L. R. Muenz, "Standardized Mood Induction with Happy and Sad Facial Expressions," Psychiatry Res., vol. 51, pp. 19-31, Jan. 1994.

C. L. Kleinke, T. R. Peterson and T. R. Rutledge, "Effects of Self-Generated Facial Expressions on Mood." J Pers Soc Psych, vol. 74, No. 1, pp. 272-279, 1998.

J. I. Davis, A. Senghas, F. Brandt and K. N. Ochsner, "The Effects of BOTOX Injections on Emotional Experience," Emotion, vol. 10, No. 3, pp. 433-440, Jun. 2010.

L. M. Schrader, I. A. Cook, P. R. Miller, E. R. Maremont and C. M. DeGiorgio, "Trigeminal nerve stimulation in major depressive disorder: First proof of concept in an open pilot trial," Epilepsy Behav., vol. 22, pp. 475-478, Nov. 2011.

I. A. Cook, L. M. Schrader, C. M. DeGiorgio, P. R. Miller, E. R. Maremont, and A. F. Leuchter, "Trigeminal nerve stimulation in major depressive disorder: Acute outomes in an open pilot study," Epilepsy Behav., vol. 28, pp. 221-226, 2013.

\* cited by examiner

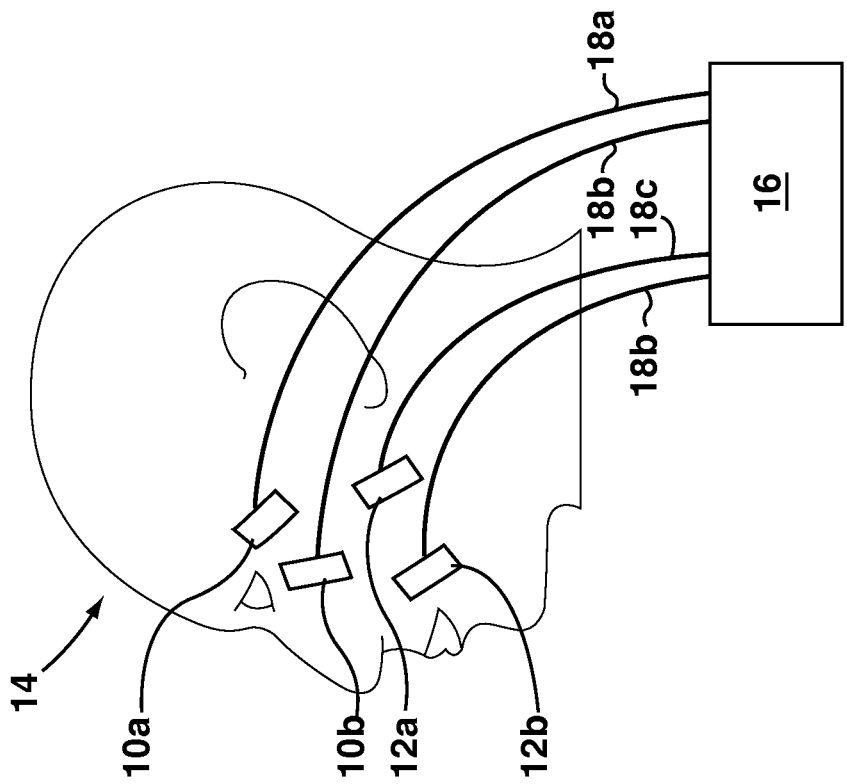
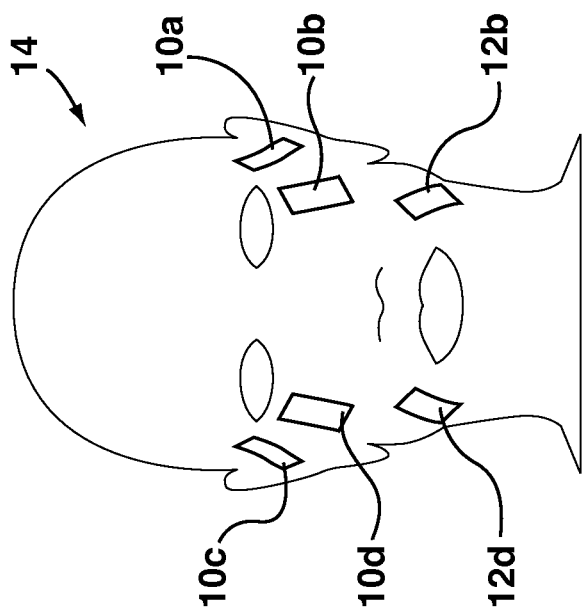
FIG. 1b
FIG. 1a

PANAS-X Items showing a statistically significant difference between the initial and final assessments, for each group of individuals. Values provided are mean ± standard deviation. NP indicates that non-parametric statistics were used, and P indicates that parametric statistics were used (see Methods section of the text).

| PANAS-X Item | Initial | Final | p-value |
|---|---|---|---|
| *Control Group* | | | |
| Base scores | | | |
| Daring | 2.83 ± 1.19 | 1.58 ± 0.67 | 0.00 (NP) |
| Lively | 2.92 ± 1.16 | 2.00 ± 0.85 | 0.00 (P) |
| Determined | 3.58 ± 1.38 | 2.67 ± 1.07 | 0.02 (NP) |
| Aggregate scores | | | |
| Positive affect | 30.83 ± 8.84 | 26.17 ± 8.83 | 0.01 (P) |
| Joviality | 23.33 ± 6.57 | 20.17 ± 7.46 | 0.00 (P) |
| Self-Assurance | 16.75 ± 4.14 | 13.75 ± 3.98 | 0.00 (P) |
| Attentiveness | 13.83 ± 3.88 | 11.25 ± 3.86 | 0.00 (P) |
| Fatigue | 8.08 ± 4.03 | 9.83 ± 4.49 | 0.04 (P) |
| Serenity | 9.42 ± 2.43 | 6.67 ± 1.61 | 0.00 (P) |
| *FES Group* | | | |
| Base scores | | | |
| Attentive | 4.08 ± 0.67 | 2.75 ± 1.14 | 0.00 (NP) |
| Tired | 2.58 ± 1.31 | 3.25 ± 0.97 | 0.02 (P) |
| Nervous | 2.00 ± 0.60 | 1.33 ± 0.49 | 0.04 (NP) |
| Concentrating | 3.75 ± 0.87 | 2.67 ± 1.23 | 0.01 (NP) |
| Aggregate scores | | | |
| Negative affect | 12.92 ± 1.93 | 11.67 ± 1.50 | 0.01 (P) |
| Fear | 8.83 ± 1.70 | 7.42 ± 1.16 | 0.00 (NP) |
| Joviality | 22.42 ± 6.46 | 19.75 ± 6.65 | 0.02 (P) |
| Self-Assurance | 14.17 ± 3.10 | 12.08 ± 3.87 | 0.00 (P) |
| Attentiveness | 13.67 ± 2.71 | 10.67 ± 3.92 | 0.00 (P) |
| Serenity | 10.25 ± 1.76 | 7.25 ± 1.22 | 0.00 (NP) |

FIG. 4

Significance of change score comparisons between the FES and control groups, for all items in the PANAS-X. A direction of change of ↑ indicates that the FES scores were higher than the control scores, whereas ↓ indicates that the FES scores were lower than the control scores. NP indicates that non-parametric statistics were used, and P indicates that parametric statistics were used (see Methods section of the text).

| | p-value | Direction | | p-value | Direction |
|---|---|---|---|---|---|
| PANAS-X Base Items | | | | | |
| cheerful | 0.93 (NP) | | active | 0.16 (NP) | |
| disgusted | 0.32 (NP) | | guilty | 0.15 (NP) | |
| attentive | 0.11 (P) | | joyful | 0.47 (NP) | |
| bashful | 0.42 (NP) | | nervous | 0.13 (NP) | |
| sluggish | 1.00 (P) | | lonely | 0.93 (NP) | |
| daring | 0.04 (P) | ↑ | sleepy | 0.84 (P) | |
| surprised | 0.19 (NP) | | excited | 0.53 (NP) | |
| strong | 0.66 (NP) | | hostile | 0.32 (NP) | |
| scornful | 0.12 (NP) | | proud | 0.45 (NP) | |
| relaxed | 0.54 (NP) | | jittery | 0.17 (NP) | |
| irritable | 0.51 (NP) | | lively | 0.26 (NP) | |
| delighted | 0.98 (NP) | | ashamed | 1.00 (NP) | |
| inspired | 0.34 (NP) | | at ease | 0.92 (NP) | |
| fearless | 0.95 (NP) | | scared | 0.03 (NP) | ↓ |
| disgusted w/ self | 0.32 (NP) | | drowsy | 1.00 (P) | |
| sad | 0.33 (NP) | | angry at self | 0.32 (NP) | |
| calm | 0.28 (NP) | | enthusiastic | 0.90 (NP) | |
| afraid | 0.40 (NP) | | downhearted | 1.00 (NP) | |
| tired | 0.71 (NP) | | sheepish | 0.17 (NP) | |
| amazed | 0.17 (NP) | | distressed | 0.45 (NP) | |
| shaky | 0.44 (NP) | | blameworthy | 1.00 (NP) | |
| happy | 0.34 (NP) | | determined | 0.03 (NP) | ↑ |
| timid | 0.30 (NP) | | frightened | 0.32 (NP) | |
| alone | 0.55 (NP) | | astonished | 0.52 (NP) | |
| alert | 0.35 (NP) | | interested | 0.78 (NP) | |
| upset | 1.00 (NP) | | loathing | 0.32 (NP) | |
| angry | 0.32 (NP) | | confident | 0.79 (NP) | |
| bold | 0.52 (NP) | | energetic | 0.09 (NP) | |
| blue | 0.93 (NP) | | concentrating | 0.04 (NP) | ↓ |
| shy | 0.62 (NP) | | dissatisfied w/ self | 0.17 (NP) | |
| PANAS-X Aggregate Scores | | | | | |
| Negative affect | 0.45 (P) | | Self-Assurance | 0.40 (NP) | |
| Positive affect | 0.34 (P) | | Attentiveness | 0.72 (NP) | |
| Fear | 0.05 (NP) | | Shyness | 0.92 (NP) | |
| Hostility | 0.24 (NP) | | Fatigue | 0.84 (P) | |
| Guilt | 0.79 (NP) | | Serenity | 0.75 (P) | |
| Sadness | 0.92 (NP) | | Surprise | 0.43 (P) | |
| Jovialit | 0.81 (NP) | | | | |

FIG. 5

FUNCTIONAL ELECTRICAL STIMULATION METHOD, USE AND APPARATUS FOR MOOD ALTERATION

CROSS-REFERENCE TO RELATED APPLICATION

The application claims benefit of co-pending U.S. Provisional Application 61/776,962, filed Mar. 12, 2013, and entitled FUNCTIONAL ELECTRICAL STIMULATION METHOD, USE AND APPARATUS FOR MOOD ALTERATION, the entire subject matter of which is incorporated herein by reference.

FIELD

The present disclosure relates to a method for altering a mood in an individual through the use of functional electrical stimulation. More particularly the present disclosure relates to the use of functional electrical facial muscle stimulation to modulate activity in the subcortical nuclei and/or cortical regions through activation of the extrapyramidal and pyramidal motor systems.

BACKGROUND

Major depressive disorder (MDD) is a condition that affects an alarmingly high number of people at some point during their lives, with a prevalence varying between 3% and 16%, depending on the country. Although a number of pharmaceutical interventions are available, some MDD sufferers are partially or completely resistant to these treatments, and it is estimated that up to 50% of patients do not achieve full remission. In addition, anti-depressant drugs have a number of side-effects, including nausea, insomnia and weight gain. Alternative and/or complementary forms of treatment for MDD are therefore needed. Additionally, it is desirable to develop methods to modulate a mood aspect or parameter of an individual without reliance on pharmaceutical interventions.

A substantial body of research has been devoted to the study of facial movements as they relate to particular emotions or moods. Facial expressions for basic emotions (happiness, fear, surprise, etc.) have been found to be well-defined and universal across cultures. Certain facial muscle movements can be easily controlled voluntarily, while others occur primarily during "genuine" emotions. For example, voluntary smiles (e.g. smiles for social purposes, without any particular emotional involvement) usually consist only of the upward curving of the lips, whereas spontaneous smiles due to positive genuine spontaneous emotions also involve the eyes. The specific pattern of eye movement associated with genuine smiling is known as the Duchenne marker, and is characterized by a raising of the cheeks and the appearance of crows-feet wrinkles next to the eyes. Different neural pathways mediate these two types of smiles.

Voluntary smiles are initiated in the motor cortex and routed via the pyramidal motor system. In contrast, involuntary smiles arise mainly from subcortical nuclei and are routed via the extrapyramidal motor system. Clinical evidence from Parkinson's patients displaying the "masked face" syndrome suggests that the basal ganglia is involved in the production of emotional expression, while evidence from patients with brain lesions exhibiting emotional facial paresis suggests the possible involvement of various regions of the basal ganglia and thalamus. Furthermore, neuroimaging studies have also substantiated the involvement of the basal ganglia. A related observation has been that voluntarily producing and holding an expression normally seen with genuine spontaneous response can induce the corresponding emotion. This effect has been linked to afferent facial feedback received as a result of the facial movements. The induction of emotion is more effective when a person pays specific attention to voluntarily activating muscles that are usually only used involuntarily (e.g., the Duchenne marker), possibly because the voluntary facial expression is then closer to a genuine one.

Functional electrical stimulation (FES) is a technique in which muscles are electrically stimulated by attaching at least two electrodes of an apparatus to a body region. Briefly, functional electrical stimulation is a technique that uses electrical currents to activate nerves connected to the central nervous system which innervate corresponding muscles to a level sufficient to elicit the motor threshold. In other words, in the practice of FES the electrical current is applied at a level to produce muscular movement of a target muscle. FES has been used to activate nerves which innervate extremities affected by paralysis resulting from spinal cord injury (SCI), head injury, stroke and other neurological disorders. FES is also sometimes referred to as neuromuscular electrical stimulation or NMES.

In the practice of FES, at least two electrodes, an anode and a cathode (complementary electrodes), are coupled to the body of an individual. The anode is placed at a region on the body to receive electrical current. Typically, the anode is placed in the vicinity of a peripheral nerve that is innervating the muscle or muscles of interest, for example termed the targeted muscle, and the cathode is placed at a convenient location to close the electrical circuit or loop such that the current can circulate the loop (a complete circuit). Furthermore, in FES, it is preferred that the current applied to the loop is not sufficient so as to cause contractions in the muscles which are not of interest, in other words the electrode pairs should be placed to ensure specificity, i.e., that only muscles of interest are contracted. Various types of electrodes are known, including surface electrodes or implantable electrodes. Furthermore, the stimulation systems may include a multichannel stimulator wherein a plurality of electrodes may be controlled to stimulate one or more muscles or regions of muscles and can be triggered by a switch or several switches or signals from one or more sensors or types of sensors. Fully implantable systems are known which may similarly provide stimulation that can be controlled by switches or sensory signals. Such FES systems may also be preprogrammed to provide the electrical stimulation in a predetermined sequence in open- or closed-loop stimulation patterns.

FES has been shown to have therapeutic applications: artificially stimulating paralyzed or weakened muscles after spinal cord injury or stroke while the individual attempts to voluntarily contract those same muscles can lead to significant functional improvements. Recent studies have shown that this process is accompanied by plasticity in the central nervous system (CNS), with regions affected by the injury and associated with the stimulated muscles displaying increased activity.

A recent pilot study used electrical stimulation of the trigeminal nerve for the treatment of depression where the electrical stimulation was delivered through the skin surface, but not to the level of functional electrical stimulation. In this study, the electrical stimulation was applied so as not to generate muscle contraction or muscle movement, but instead to stimulate a peripheral nerve to evoke sensation or to neuromodulation of the central nervous system. Furthermore, the trigeminal nerve stimulation was not accompanied by any voluntary movement.

Numerous previous studies have demonstrated the close link between emotion and facial expression. This link is well supported by neuroimaging studies and clinical evidence. It would be desirable to alter the mood or a mood aspect of an individual by exploiting the link between emotion and facial expressions through the use of FES to modulate the neural pathways underlying a given emotion. For example, rather than alter the activity of the neural circuits directly responsible for MDD, which are widespread and not fully understood, an approach may be to directly modulate a mood aspect or parameter of an individual. It would be desirable to use functional electrical stimulation as a means to stimulate facial muscles and by doing so generate desired facial expressions associated with genuine emotions so as to evoke such emotions in the central nervous system and consequently to alter a given mood parameter of an individual so as to alter the overall mood of the individual.

Deep-brain stimulation (DBS) and transcranial magnetic stimulation (TMS) are other electrical modalities currently being explored for the treatment of psychiatric disorders. The application of FES to facial muscles to alter the overall mood of an individual is appealing from a standpoint that it is simultaneously non-invasive (unlike DBS) and precisely targeted (unlike TMS); and, unlike prior uses of electrical stimulation can be employed to activate specific muscles or muscle groups. Therefore FES can be used to generate a very specific facial expression representative of a mood that is desired to be evoked in an individual. The central nervous system (CNS) and muscles are a very tightly coupled system and therefore the emotional state of the CNS of an individual may be reflected outwardly in the muscle contraction levels/activity associated with emotion. Similarly, changes in the activity of various muscles may influence the state of the CNS. By artificially generating facial expressions that are tightly coupled with particular emotions, the emotional state of the individual may be altered.

SUMMARY

The following presents a simplified summary of the general inventive concept herein to provide a basic understanding of some aspects of the invention. This summary is not an extensive overview of the invention. It is not intended to restrict key or critical elements of the invention or to delineate the scope of the invention beyond that explicitly or implicitly described by the following description and claims.

In one aspect, there is provided a method of functional electrical stimulation for activating one or more neural tracts associated with the pyramidal and/or extrapyramidal motor systems comprising stimulating at least one orbicularis oculi muscle through a plurality of electrodes attachable to facial regions of an individual. In certain exemplary embodiments, the method includes activating one or more neural tracts associated with the pyramidal and/or extrapyramidal motor systems by stimulating at least one zygomatic major muscle through the plurality of electrodes attachable to the facial regions of the individual.

In some exemplary embodiments, the method comprises the use of functional electrical stimulation for activating one or more neural tracts associated with the pyramidal and/or extrapyramidal motor systems to effect a mood parameter change, said method comprising:

a) providing an electric current to the facial regions of the individual through the plurality of electrodes attachable to said facial regions for stimulating the at least one orbicularis oculi muscle and the at least one zygomatic major muscle;

b) electrically stimulating the at least one orbicularis oculi muscle;

c) electrically stimulating the at least one zygomatic major muscle; and d) discontinuing the electric stimulation of the at least one orbicularis oculi muscle and the at least one zygomatic major muscles so as to effect relaxation of the at least one orbicularis oculi muscle and the at least one zygomatic major muscle.

According to some exemplary embodiments, the electrical stimulation is applied at level sufficient to elicit the motor activation threshold. The electrical stimulation is applied to a point where contraction of the muscle can be visually seen or, in some exemplary embodiments to a point where muscular contraction can be detected by palpation.

According to certain exemplary embodiments, steps a) to d) of the method are repeated at least 5 times. In some exemplary embodiments, steps a) to d) are repeated about 25 times over the course of about one hour.

In some exemplary embodiments of the method, the electrical current is provided as a plurality of biphasic pulses with each one of said biphasic pulses having an amplitude of from about 1 mA to about 15 mA. In some exemplary embodiments, each biphasic pulse is provided with an amplitude of from about 1 mA to about 10 mA.

According to certain exemplary embodiments, the plurality of biphasic pulses are delivered at from about 16 Hz to about 100 Hz. In some exemplary embodiments, the plurality of biphasic pulses are delivered at about 20 Hz to about 60 Hz.

In some exemplary embodiments, the plurality of biphasic pulses is delivered for a time period of at least 1 second.

In some exemplary embodiments, each biphasic pulse is delivered for a duration of from about 25 µsec to about 1,000 µsec. In some exemplary embodiments, each biphasic pulse is delivered for a duration of about 150 µsec to about 400 µsec.

In some exemplary embodiments the plurality of electrodes are provided to electrically stimulate both orbicularis oculi muscles located bilaterally on the face of the individual. Furthermore, in some exemplary embodiments the plurality of electrodes are also provided to electrically stimulate both zygomatic major muscles located bilaterally on the face of the individual.

In some exemplary embodiments, the use of the functional electrical stimulation modulates the activity of subcortical nuclei activity through the extrapyramidal motors system and/or cortical brain region activity through the pyramidal motor system related to an associated given emotion. In some exemplary embodiments, the use functional electrical stimulation is provided to produce a Duchenne marker by electrically stimulating the orbicularis oculi muscles and the zygomatic major muscles using a plurality of electrodes attachable to facial regions of an individual.

In another aspect, there is provided an apparatus comprising a multi-channel stimulator for use in performing the method as hereinabove defined. In some exemplary embodiments, the multi-channel stimulator is preprogramed to automatically and repeatedly provide steps a) to d) of the method in a sequential manner to the individual having the plurality of electrodes in operable communication with a their facial regions.

In another aspect, there is provided a kit for performing mood altering functional electrical stimulation. The kit comprises a multichannel stimulator apparatus; a plurality of electrodes for delivering functional electrical stimulation from the apparatus to an individual; and instructions for electrode placement on the individual and apparatus use. In some exemplary embodiments, the multi-channel stimulator is preprogramed to automatically and repeatedly provide steps a) to d) of the method to the individual connected thereto in a sequential fashion.

In yet another aspect, a use of functional electrical stimulation for altering a mood of an individual comprising electrically stimulating at least one facial muscle associated with a first mood so as to activate one or more neural tracts associated with the extrapyramidal and/or pyramidal motor systems is provided. In some exemplary embodiments, at least one mood aspect associated with major depressive disorder is altered. Furthermore, in some exemplary embodiments, the use functional electrical stimulation produces a Duchenne marker. According to some exemplary embodiments, the use of functional electrical stimulation is provided for treating major depressive disorder. In some exemplary embodiments, at least one facial muscle associated with a mood is stimulated so as to modulate the activity of subcortical nuclei through the extrapyramidal motor system and/or cortical brain region activity through the pyramidal motor system.

In another aspect, there is provided an apparatus for functional electrical stimulation. The apparatus comprises plurality of complementary electrodes for attachment to a facial region of an individual and means for providing an electric current to the region through said electrodes to effect functional electrical stimulation. In some exemplary embodiments the electric current is provided as a plurality of biphasic pulses having a frequency of from about 16 Hz to about 100 Hz. Additionally, the biphasic pulses have an amplitude of from about 1 mA to about 15 mA. In some exemplary embodiments, the plurality of biphasic pulses have a frequency of about 20 Hz to about 60 Hz and an amplitude of from about 1 mA to about 10 mA.

The apparatus, in some exemplary embodiments, includes a multi-channel stimulator capable of being programmed for providing the electric current to the plurality electrodes in a predetermined and preprogrammed sequence. In some exemplary embodiments, the stimulator is programmable to automatically deliver the biphasic pulses in a user-configurable pattern. Additionally the plurality of electrodes may be surface electrodes or implantable electrodes.

In another exemplary embodiment, there is provided a method for treating a subject having a condition associated with a mood or an emotional state. The method comprises applying electrical stimulation to at least one facial muscle associated with the mood or emotional state to activate one or more neural tracts of the extrapyramidal and/or pyramidal motor systems of the subject, thereby altering a mood parameter or emotional state of the subject.

In some exemplary embodiments, the subject is afflicted with major depressive disorder, and said method improves a mood parameter or emotional state of the subject.

In some exemplary embodiments, the method may include instructing the individual to perform the voluntary smile expression, while applying stimulation.

In some exemplary embodiments, the electrical stimulation may be applied using a pair of electrodes attached to the face of the subject to cause electrical flow along a facial muscle, thereby to trigger the muscle. In some cases, more than one type of facial muscle may be stimulated.

In some exemplary embodiments, the electrical stimulation may trigger Duchenne marker.

In some exemplary embodiments, the facial muscle type may be selected from a zygomatic major muscle, an orbicularis oculi muscle, and both said muscles, and/or electrical stimulation may be applied to two orbicularis oculi muscles through a corresponding number of electrode pairs.

In some exemplary embodiments the method may comprise:
a. placing electrode pairs on the face of the subject to establish an electric circuit along at least one orbicularis oculi muscle and along at least one zygomatic major muscle;
b. electrically stimulating the at least one orbicularis oculi muscle;
c. electrically stimulating the at least one zygomatic major muscle; and
d. discontinuing the electrical stimulation to allow the muscles to relax.

In another exemplary embodiment, there is provided a system for use in mood altering functional electrical stimulation to a facial region of a person. The system comprises a multi-channel stimulator configured to electrically stimulate more than one muscle in the facial region through electric current provided to a pair of electrodes; with each muscle to be stimulated through a separate channel, in a coordinated fashion.

In some exemplary embodiments, the multi-channel stimulator is configured to provide an electric current to said facial regions of said individual through said plurality of electrodes attachable to the facial regions for stimulating at least one orbicularis oculi muscle and at least one zygomatic major muscle, to:
a) electrically stimulate the at least one orbicularis oculi muscle;
b) electrically stimulate the at least one zygomatic major muscle; and
c) discontinue said electrical stimulation of the at least one orbicularis oculi muscle and the at least one zygomatic major muscle so as to effect relaxation of the at least one orbicularis oculi muscle and the at least one zygomatic major muscle.

In some exemplary embodiments, methods herein may further comprise, in advance of applying electrical stimulation, detecting a voluntary smile. In this case, the detecting a voluntary smile may include measuring electromyography of a first set of one or more selected face muscles. The applying may be directed at the first and/or a second set of one or more selected face muscles. The detecting a voluntary smile may also or alternatively, include a microphone.

BRIEF DESCRIPTION OF THE DRAWINGS

In order that the invention may be better understood, embodiments will now be described by way of example only, with references to the accompanying drawings wherein:

FIG. 1a is a frontal view schematic representation of an individual's face showing the placement of bipolar stimulating electrodes located bilaterally to stimulate the orbicularis oculi and zygomatic major muscles;

FIG. 1b is a sagittal view schematic representation of the individual's face of FIG. 1a showing the placement of bipolar stimulating electrodes located bilaterally to stimulate the orbicularis oculi and zygomatic major muscles and connected to a multichannel functional electrical stimulation apparatus;

FIG. 4 is a table showing differences between the initial and final mood parameter assessment scores for various statistically significant mood parameters in the FES and control groups;

FIG. 5 is a table showing the statistical significance of the change scores comparison between the FES and control groups for all mood parameters assessed.

DETAILED DESCRIPTION

Figure 2:
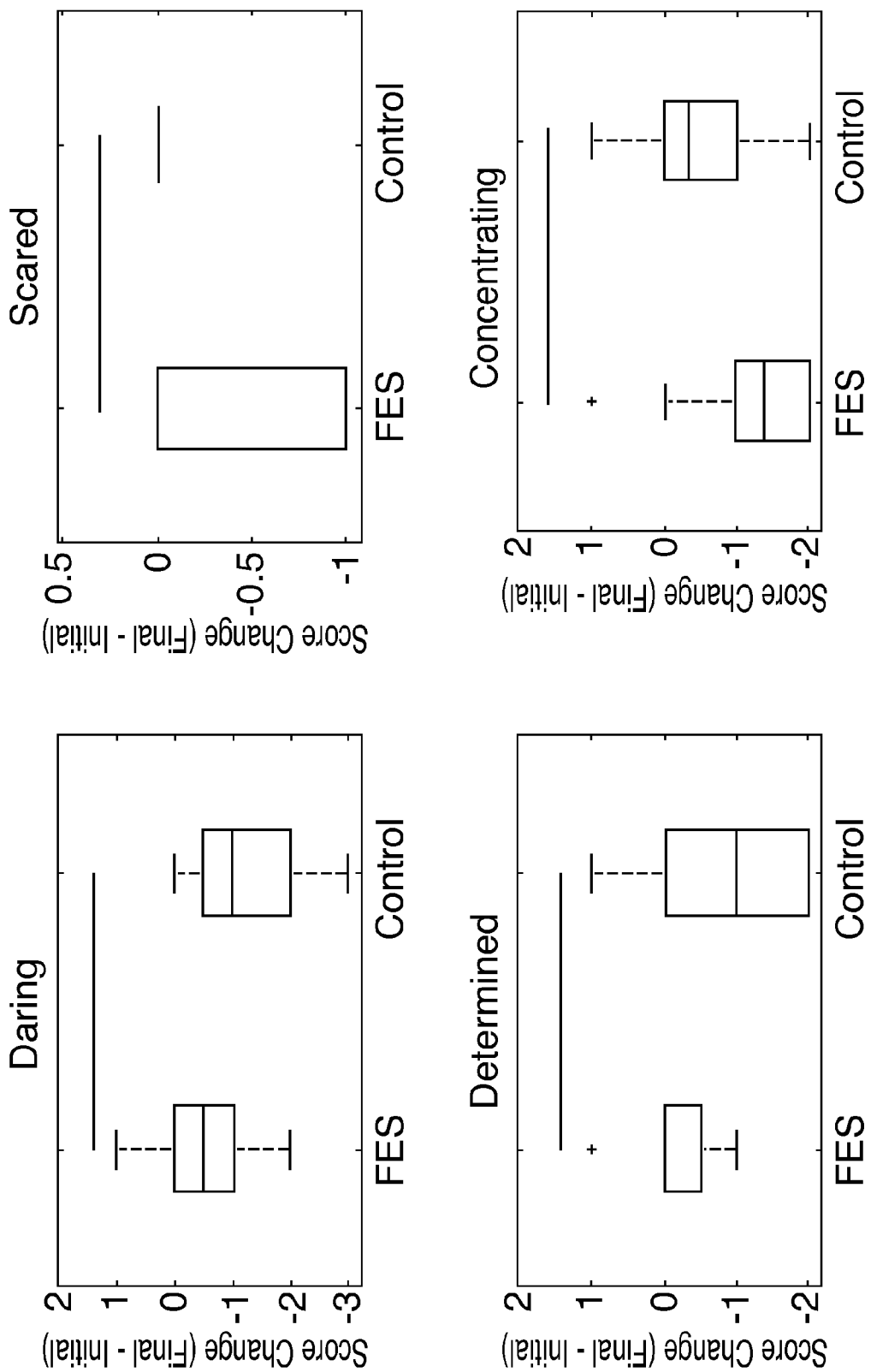
FIG. 2 shows boxplots of mood parameter assessment change score distributions for the FES and control groups in outcomes having statistical significance.

The method described herein is provided for altering the mood of an individual using functional electrical stimulation (FES). Briefly, it has been found that stimulating, in particular facial muscles that are associated with various mood-related facial expressions, one can alter various mood parameters and thus contribute to altering the overall mood of an individual. For example, it has been found that stimulation of facial muscles associated with spontaneous genuine facial expressions may have an effect on mood assessment parameters by an individual that has received the functional electrical stimulation. The method, and use, is based on the surprising discovery that by stimulating facial muscles associated with genuine facial expressions, subcortical nuclei and cortical activity in the brain is modulated through involvement of the extrapyramidal and/or pyramidal motor systems.

Accordingly, a new method, and use of FES has been found. The method relates to improving, or altering, the mood of an individual by administering FES to the individual in a coordinated fashion that mimics the natural facial muscle patterns of a given genuine emotion. In certain complex mood-associated disorders, such as for example, major depressive disorder, various mood aspects mood parameters (feelings) of the individual maybe ameliorated or otherwise altered. In some exemplary embodiments the individual is directed to voluntarily exercise the same facial movement (i.e., the execution of the same genuine functional facial movement) in a time-synchronized manner along with the stimulation, thereby enhancing the electrical stimulation input with a biological activity.

Although a method of facial stimulation is known, it does not involve stimulating neural pathways associated with emotion, or use FES to evoke facial expressions associated with emotions.

In general terms, the method comprises stimulating facial muscles that are required for an individual to produce a voluntary (or involuntary, in the case of a genuine emotion) movement associated with a given mood using FES such that the extrapyramidal and/or pyramidal motor systems are utilized to modulate subcortical nuclei and/or cortical brain activity.

In an exemplary embodiment, moods or mood aspects associated with major depressive disorder may be improved by functionally electrically stimulating facial muscles associated with genuine emotions using a multi-channel functional electrical stimulation apparatus 16. Additionally, the multichannel functional electrical stimulation apparatus 16, in some exemplary embodiments, may be preprogramed to automatically provide mood altering functional electrical stimulation to an individual connected thereto in a coordinated fashion. For example, electrodes are used to stimulate facial muscles associated with the Duchenne marker. In such an example, a first set of electrodes 10a and 10b are placed as shown in FIGS. 1a and 1b so as to, upon activation by the apparatus 16, stimulate the orbicularis oculi muscle of an individual 14. As second set of electrodes 12a and 12b are placed, also as shown in FIGS. 1a and 1b, so as to, upon activation by the apparatus 16, stimulate the zygomaticus major muscle (zyomatic major muscle) of the individual 14. Electrodes 10c and 10d, as shown in FIGS. 1a and 1b may also be placed to provide stimulation the orbicularis oculi muscle on the opposing side of the individual's face as well as electrodes 12c (not shown) and 12d to stimulate the zygomaticus major muscle. The electrodes are connected to the multi-channel functional electrical stimulation apparatus 16, by way of corresponding wires or cables 18a, 18b, 18c, 18d as is shown, for example in FIG. 1b. However, one of skill in the art will readily appreciate that any number of electrodes and corresponding wires may be used dependent on the number of muscles desired to be stimulated and the number of channels on the multi-channel functional electrical stimulation apparatus 16. The method then involves the coordinated functional electrical stimulation of the orbicularis oculi muscles and zygomaticus major muscles to produce the Duchenne marker. Therefore, in one exemplary embodiment the method involves:

a) electrically stimulating at least one orbicularis oculi muscle;

b) electrically stimulating at least one zygomatic major muscle; and c) relaxing the at least one orbicularis oculi muscle and the at least one zygomatic major muscle.

Accordingly, in some exemplary embodiments, the method for activating one or more neural tracts associated with the extrapyramidal and/or pyramidal motor systems to effect a mood parameter change in an individual involves:

a) providing an electric current to facial regions of an individual through a plurality of complementary electrodes attachable to said facial regions for stimulating at least one orbicularis oculi muscle and at least one zygomatic major muscle;

b) electrically stimulating the at least one orbicularis oculi muscle;

c) electrically stimulating the at least one zygomatic major muscle; and d) discontinuing the electrical stimulation of the at least one orbicularis oculi muscle and the at least one zygomatic major muscle so as to effect relaxation of the at least one orbicularis oculi muscle and the at least one zygomatic major muscle.

Furthermore, in some exemplary embodiments, both orbicularis oculi muscles and zygomatic major muscles in a face of an individual may be stimulated.

In accordance with the method, steps a) to d), noted above, may be repeated at least 5 times. In some exemplary embodiments, steps a) to d) are repeated about 25 times over the course of a one hour period.

As the method is believed to act by activating the extrapyramidal and/or pyramidal motor systems associated with various emotions so as to modulate activity in the subcortical nuclei and/or cortical structures, the amplitude of the electrical stimulation may be determined on the basis of stimulation sufficient to cause a visible contraction or contraction detectable by palpation in the target muscles. Therefore, the amplitude of the electrical stimulation may be set at a level sufficient to cause a visible contraction in the desired muscle, while avoiding unnecessary pain to the individual or excessive movement of the target muscle. For example, the electrical stimulation delivered is sufficient so as to elicit activation of the motor threshold in the target muscle. That being the electrical stimulation is provided such that a contraction of the target muscle or muscles can be visibly seen or the contraction can be detected by palpation.

Various electrical stimulation amplitude levels and pulse types may be used, or required, so as to produce muscle movements associated with various emotions. In the case of the exemplary embodiment noted above, a plurality of biphasic pulses are delivered at from about 16 Hz to about 100 Hz and with each one of said biphasic pulses having an amplitude of from about 1 mA to about 15 mA may be used. In some exemplary embodiments, the plurality of biphasic pulses are delivered to the electrodes, and consequently the individual, at 20 Hz to about 60 Hz and an amplitude of from about 1 mA to about 10 mA.

Furthermore, dependent on the emotional facial movement desired to be mimicked by the use of the functional electrical stimulation, each biphasic pulse may be delivered for a duration of from about 25 μsec to about 1000 μsec. In some exemplary embodiments, each biphasic pulse is delivered for a duration of about 150 μsec to about 400 μsec.

In the execution of the method of the invention, a functional electrical stimulation apparatus is used, as noted herein. The FES apparatus may include a single channel stimulator to provide the electrical current to the plurality of electrodes, however in some exemplary embodiments a multi-channel stimulator is used. For example, the multi-channel stimulator may be capable of providing the electrical current to a plurality of complementary electrode pairs, comprising an anode and a cathode, where each pair of electrodes is connected to a stimulator for stimulating a region of the face of the individual by providing electric current thereto. Accordingly, a variety of stimulators were made, having at least two channels, but in some exemplary embodiments, more channels are preferred. For example, a first channel may be provided for providing electric current to a first orbicularis oculi muscle and a second channel may be provided for providing electric current to a second bilaterally opposed orbicularis oculi muscle through the electrodes when attached to an associated facial region of the individual. A third channel may be provided for providing electric current to a first zygomatic major muscle and fourth channel may be provided for providing electrical current to a second bilaterally opposed second zygomatic major muscle through the electrodes when attached to an associated facial region of the individual. Therefore, in some exemplary embodiments, a four-channel stimulator was used. However, in the execution of the method more than two or four channels may be desirable and used depending on the number of facial muscles associated with a mood aspect to which the method is employed.

In some exemplary embodiments, the stimulator is preprogramed to provide electric current to the various channels in a predetermined sequence. In some embodiments the electric current is provided to the various channels as biphasic pulses with a frequency of from about 16 Hz to about 100 Hz and preferably about 20 Hz to about 60 Hz. Furthermore, the electric current is provided with an amplitude of from about 1 mA to about 15 mA and preferably from about 1 mA to about 10 mA. The level of the amplitude may also be user-configurable and set to only provide enough electrical current that a muscle can be visually seen to contract or contraction detectable by palpation and minimize discomfort to the individual.

Additionally the plurality of electrodes may be surface electrodes or implantable electrodes. Furthermore, the entire system or components thereof may be surface-located or implantable. For example, in some exemplary embodiments, the electrodes, cables connecting the electrodes to the stimulator and the stimulator may be implanted in an individual. In another exemplary embodiment, the electrodes may be implanted in the individual and the stimulator located external to the individual's body with the cables connecting the electrodes to the stimulator traversing therebetween. In another exemplary embodiment, the electrodes may be surface electrodes and the cables connecting the electrodes to the stimulator and the stimulator itself may all be located external to the individual's body.

Therefore the multi-channel FES apparatus allows for the targeting of individual muscles, as required, and is enabled so as to be programmable to provide electrical current to said individual muscles during the execution of various facial expressions associated with different mood aspects or parameters, for example the production of the Duchenne marker.

In some exemplary embodiments, such as the method of the example discussed below, the stimulator was preprogramed to provide the stimulation pattern in accordance with the exemplary method below and allowed for user-provided input with regard to the amplitude of the electric current pulse. However, the stimulator may be preprogramed to provide various durations for supplying electric current to the electrodes as well as the sequence to which the electric current is provided to the electrodes and the length of a protocol. Once programmed and the electrodes are attached to the facial regions of the user, a program to execute a facial expression associated with mood aspect or parameter can be selected by a user and the amplitude set as indicated above. The device may then automatically cycle through the protocol selected so as to provide a consistent regime of stimulation to the individual.

In one possible modification of the apparatus, the stimulator could communicate with an input means for the individual, such as a card containing a radio frequency identification chip, or USB fob, or numeric patient identifier code identifying an individual. Thus the individual may have a personalized routine set up for them, and programmed onto the card or fob, which communicates with the device to select a desired protocol of facial muscle stimulation. It would be understood that the device could be supplied with a variety of such individual input means, each having a protocol or series of protocols preprogramed, or each being blank so as to be programmed by a user.

Figure 6:
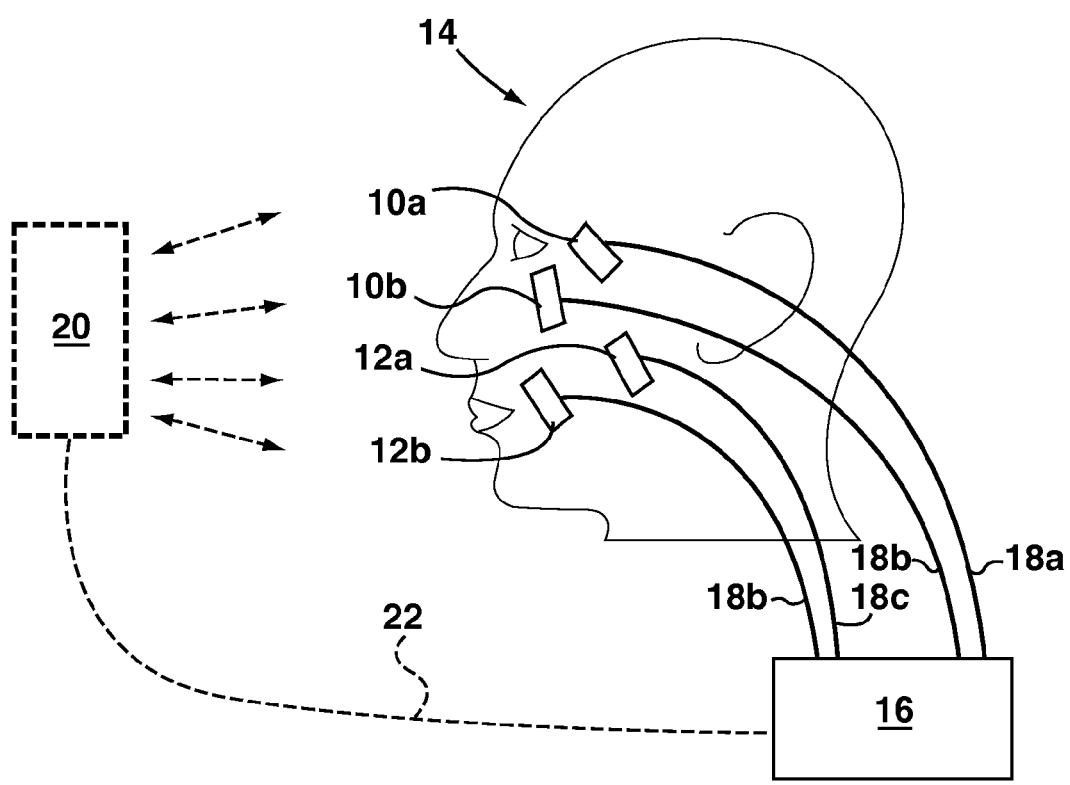
FIG. 6 is a sagittal view schematic representation showing an alternative configuration to that shown in FIG. 1b.

Referring to FIG. 6, exemplary embodiments of the method may also be deployed following a previous indication, or initiation of a "voluntary" smile. For instance, a step may be undertaken to measure electromyography [EMG] (schematically represented by an EMG device shown at 20 (for example the AMT-8 EMG system available from BORTEC BIOMEDICAL LTD. (www.bortec.ca)), of a first set of one or more selected face muscles, such as the orbicularis oculi and/or zygomatic major. The patient may then be instructed to voluntarily smile (or laugh), thus indicating a contraction of the muscle(s). In this case, on indication of the voluntary smile by the EMG device 20, via path 22, one or more of the FES steps described herein may then be employed to initiate FES, as explained herein, to activate further muscle contractions. In this manner, voluntary initiation of a smile by the subject may be implemented as a precursor to a later protracted and "stronger" smile, by the subject, by contracting a set of one or more selected first face muscles, as described herein, and then activating contraction of one or more selected of the first muscles or a set of one or more selected second face muscles, thereby providing a neuro-feedback and/or an enhanced neuromodulation system.

Similarly, in place of, or in combination with EMG detection, the voluntary smile may be detected instead by a voluntary smile or chuckle, as detected by a microphone, or by a gesture sensing device such as a video image capture system or the like, as represented by 20 in FIG. 6 (such as the Nuidroid Face facial gesture system (www.nuidroid.com)).

In some exemplary embodiments, the method may include instructing the individual to perform the voluntary smile expression, during while the corresponding stimulation is applied, without necessarily using sensors or the like to detect or to trigger the stimulation. This may then provide the benefit of pairing the voluntary activity with the stimulation.

Provided below is an exemplary experimental protocol and results in accordance with method and apparatus presented above.

EXAMPLE 1

The ability of a single session of FES to modulate positive aspects or parameters of mood and emotion was investigated. The effectiveness of FES in other applications appears to be enhanced when the individual voluntary attempts to move the target muscles at the same time as they are being stimulated. It is believed that this is due to Hebbian plasticity, occurring at the synapses where the efferent voluntary commands meet the afferent antidromic action potentials produced by the FES. The individuals receiving FES in the study outlined below were therefore instructed to attempt to voluntarily activate the stimulated muscles (see stimulation details below). In order to discriminate between the effects of the FES and the effects of voluntarily holding a facial expression, a control group was used, which performed the same experimental procedures as the FES group but without any stimulation.

The effects of instant experimentation where analyzed through the use of standardized questionnaires (see Assessment below). Accordingly, since it was likely that the individual's self-assessment would be skewed if they were aware of the true purpose of the experiment a deception portion was used in the experimental design. A mock experiment was designed that allowed for the collection of data required to evaluate the effectiveness of FES in altering the mood of an individual while presenting the individuals with a different rationale for the procedures. Individuals were told that the goal of the experiment was to investigate applications of FES in Bell's palsy (a form of facial paralysis). FES has previously been applied in this context in other studies. Although some applications of FES involve stimulating areas where sensation is impaired (e.g., below the level of spinal cord injury), this is usually not the case in Bell's palsy. Therefore the individuals were told that the experiment was to investigate whether distraction related to the sensations caused by FES during facial stimulation (mild to moderate pain) had any impact on cognitive function. The assessments were justified to the individuals by citing links between emotional state and performance in cognitive tests. The Research Ethics Board of the Toronto Rehabilitation Institute approved the study design, and all applicable institutional and governmental regulations concerning the ethical use of human volunteers were followed.

Twenty-six able-bodied individuals were recruited for the study, and divided randomly into FES and control groups. These individuals were drawn from the community and self-reported not to be suffering from any mood disorders (i.e., the exclusion criteria that were presented and emphasized to the individuals included "Individuals currently suffering from a diagnosed mood disorder or brain disorder"). One individual in each group had to be excluded. In one case because the deception was not effective (i.e., the individual guessed the true purpose of the experiment), and in the other case because the individual was not able to reliably and voluntary activate the orbicularis oculi to form a Duchenne smile. Thus, 12 individuals per group remained for analysis. The total sample contained 12 males and 12 females, with a mean age of 31.2+/−9.1 years; the FES group contained 7 males and 5 females with a mean age of 26.7+/−5.6, and the control group contained 5 males and 7 females with a mean age of 35.3+/−9.7.

At the beginning of the session, individuals were given specific instructions on how to voluntarily perform the Duchenne smile ("raise your cheeks, then let your lip corners come up"), and were allowed to practice with guidance from the investigator. The individuals then sat in front of a computer screen, and were required to perform 3 different tasks in the alternating order as noted below. Each task lasted 30 seconds and the 2-minute block was repeated 25 times in the course of a one-hour session, with short breaks after 10 and 20 blocks. The cognitive component of the tasks was implemented using a visual n-back test, a common method to produce a cognitive load for experimental purposes. In this test, a sequence of symbols is presented, and the individual is required to press a button when a symbol appears that had previously appeared exactly n steps before in the sequence. In this study, n was set to 0, 1 or 2 in alternating blocks.

For the FES group, the tasks were as follows:
1. Produce a continuous voluntary smile while receiving FES (no cognitive task).
2. Retain a neutral expression while performing the cognitive task.
3. Produce a continuous voluntary smile while performing the cognitive task and receiving FES.
4. Retain a neutral expression while performing the cognitive task.

Since 2 of the 4 tasks involve FES, the FES group individuals received a total of 25 minutes of FES during the course of the 50-minute experiment. The goal of Task 1 (voluntary smile with no cognitive task) was to ensure that the FES group spent at least a portion of the session focusing entirely on assuming the correct expression, without the distraction of the cognitive test. To justify this procedure in the context of our deception (cognitive impact of FES for facial palsy), individuals were told that the goal was to give them breaks from the cognitive test while still replicating a clinically realistic amount of FES delivery. The neutral expression task was repeated to provide regular breaks from the FES and to ensure that the individuals remained comfortable.

For the control group, the same tasks were used, with the exception that FES was not applied during tasks 1 and 3. Individuals were still instructed to perform the voluntary smile.

FES was delivered using Compex Motion stimulators (Compex SA, Switzerland). Bipolar surface adhesive electrodes measuring 2.5 cm by 1.25 cm (Nikomed USA Inc., USA) were placed bilaterally on the zygomatic major and orbicularis oculi muscles, as shown schematically in FIGS. 1a and 1b, which were stimulated simultaneously. 150 µs biphasic pulses were delivered at 60 Hz, with amplitudes in the 3-9 mA range. The pulse duration and stimulation frequency were chosen based on preliminary stimulation attempts during the protocol development stage. Amplitudes were determined for each individual at the beginning of the session, with the objective of producing visible contractions in the target muscles while avoiding unnecessary pain to the individual or excessive movement (e.g. complete closing of the eye). The zygomatic major and orbicularis oculi are the two muscles required to produce an expression of genuine happiness of the type that an individual makes spontaneously and involuntarily according to the Facial Action Coding System (FACS). Only orbicularis oculi muscle contraction is specific to genuine smiles whereas an individual in both voluntary and spontaneous smiles contracts the zygomatic major muscle. Activation of the correct facial muscles was monitored throughout the experiment by the investigator, for both the FES and control groups.

The individuals were interviewed at the end of the session in order to ascertain whether or not the deception was effective, and then informed of the true purpose of the experiment.

Assessments

The Positive and Negative Affect Schedule—Expanded Form (PANAS-X,) was administered before and after the experimental session (before the deception was revealed). This assessment asks the individual to rate 60 words or expressions that describe feelings and emotions on a scale of 1 to 5, depending on how strongly the expression describes their current state ("not at all" to "extremely"). In addition, aggregate scores are defined by combining several of the 60 base items. The primary outcomes for this study were the PANAS-X scores for "happy" (base item), "joviality" (aggregate score comprising "happy", "joyful", "delighted", "cheerful", "excited", "enthusiastic", and "lively"), and "positive affect" (aggregate score comprising "active", "alert", "attentive", "determined", "enthusiastic", "excited", "inspired", "interested", "proud", "strong"). All other components of the PANAS-X were considered secondary outcomes.

In addition, a spatial reasoning test, the Water-Level Task was administered. The Water-Level Task is a short pen-and-paper assessment that is unlikely to produce strong emotional reactions in the individuals (e.g., frustration) and skew other assessments. Although the Water-Level Task was not an outcome in the study, it was included to strengthen the deception: the presence of a cognitive assessment was expected give the study rationale that was provided to the individuals, and the presence of a second assessment was provided to make it less obvious to the individuals that the PANAS-X was the crucial outcome. Similarly, the computerized n-back test was performed only as part of the deception, and the performance on this test was not used as an outcome in our study.

Lastly, the individuals in the FES group were asked to rate the pleasantness/unpleasantness of the stimulation session on a 5-point Likert scale (Question: "Please rate the pleasantness or unpleasantness of the FES stimulation out of 5, with 1 being "very unpleasant" and 5 being "very pleasant"").

For each comparison, a Lilliefors test for normality was applied to each of the groups being compared. In within-group comparisons, if both sets of values were found to have a normal distribution, a paired t-test was applied, otherwise a Wilcoxon test was used. In between-group comparisons, if both groups were found to have a normal distribution, an unpaired t-test was applied; otherwise a Kruskal-Wallis test was used. Statistical significance was defined as $p<0.05$.

Results

The PANAS-X scores (base items and aggregate scores) were used to perform three comparisons: initial vs. final scores in the control group, initial vs. final scores in the FES group, and change in scores (final minus initial) in the FES group vs. the control group. In case of missing values due to accidentally incomplete forms (2 instances out of 2,880 base item scores), initial and final values of the missing items were assumed to be equal.

Comparison of Initial and Final Assessments

A list of the PANAS-X items that were significantly different before and after the experiment is provided in FIG. 4, for both the control and FES groups. These results reflect changes that occurred as a result of the experimental procedures, and are therefore a combination of the effects of the voluntary facial expressions, cognitive task, and FES (for the FES group). Both groups showed significant differences in several of the PANAS-X base items and aggregate scores. The scores decreased in all cases except for "tired" and "fatigue", which increased.

Comparison of FES and Control Groups

It is evident from the table of FIG. 4 that the experimental procedures themselves had a substantial effect on the moods of the participants, whether or not FES was used. Therefore, in order to better isolate the effects of the FES, the table of FIG. 5 shows the results of the change score comparisons between the control and FES groups, for all base items and aggregate scores in the PANAS-X. Significant differences were found for the mood aspects of "daring" (increase in FES group), "scared" (decrease in FES group), "determined" (increase in FES group), and "concentrating" (decrease in FES group). The change score distributions of these outcomes for both groups are shown in the boxplots of FIG. 2. A decrease in the "fear" aggregate score also very narrowly missed statistical significance ($p=0.0535$, with a median change of $-1$ and a range of $-3$ to 0 in the FES group, compared to a median change of $-0.5$ and a range of $-2$ to 2 in the control group) as can be seen in FIG. 5. The change score distributions for our primary outcomes of "happy", "joviality", and "positive affect" are provided in FIG. 3. Although some qualitative differences can be observed, particularly in "happy", for which the FES group showed a much broader distribution, none of the comparisons in FIG. 3 reached statistical significance.

FES Sensation

When asked to rate the pleasantness or unpleasantness of the FES sensation, the FES group reported a mean score of $3.08\pm0.76$. In other words, the individuals on average reported finding the sensation "neither pleasant nor unpleasant".

The above example shows a use of FES to modulate activity in neural pathways responsible for regulating emotion. Although the experimental procedures themselves had an impact on the reported mood of the individuals (with or without FES), significant differences were nonetheless found between the FES group and the control group in several of the secondary outcomes related to various moods. No significant differences were found for the primary outcomes therefore suggesting that FES may be used to modulate one or more aspects or parameters underlying a generalized mood description which may be associated with major depressive disorder.

Most of the changes occurring between the initial and final assessments in both groups are consistent with the nature of the experiment, which required the individuals to concentrate continuously on a repetitive cognitive task. Decreases in PANAS-X items such as "lively", "attentiveness", "serenity", "concentrating" and increases in "fatigue" and "tired" are therefore not surprising in light of the cognitive tasks applied as part of the deception techniques employed in the experimental design. Differences between the two groups, on the other hand, may be attributed specifically to the FES rather than the experimental procedures. The effects of the FES on mood may be mediated through the neural pathways relating emotion to facial expression, or through a reaction to the sensory signals produced by the stimulation that may in turn activate subcortical nuclei of the brain. The decrease in "concentrating" as a result of the FES does not have an obvious link with the specific facial expressions used in the experiments, but is consistent with the additional distraction caused by the FES sensation. The increases in "daring" and "determined" and the decreases in "scared", on the other hand, may be linked to short-term plasticity in the neural pathways of emotion. Although the above aspects were not the generalized emotions that the experiment aimed to elicit, the orbicularis oculi motion that the individuals performed (slight narrowing of the eyes) is consistent not only with the Duchenne smile but is also closely related to the stereotypical expression of determination. It is also worth noting that "daring", "determined", and "scared" are all related emotions, making it unlikely that the results are due simply to type 1 errors in the sample. The decrease in "fear", which was very close to statistical significance, is also inline with this analysis. The results therefore show that FES may be used to modulate brain regions involved in the facial expression of emotion and alter the mood, or aspects thereof, of an individual. An alternative interpretation for the "scared" and "fear" results is that the individuals in the FES group were more initially apprehensive about the experiment than the control group, because they knew that they were about to receive stimulation. Thus, after the experiment was over, the FES group experience a greater decrease in "scared" and "fear" than the control group. This interpretation is also supported by data presented in FIG. 4, which shows an initial vs. final decrease in "fear" in the FES group but not the control group. Nonetheless, this explanation cannot account for the between-group differences in "determined" and "daring", which are still therefore most likely a result of the FES. Indeed, if the FES group individuals had been more determined initially because of the anticipated challenge of the FES, their determination scores would have decreased more than that control group's by the end of the experiment, whereas in fact the opposite trend was observed.

Figure 3:
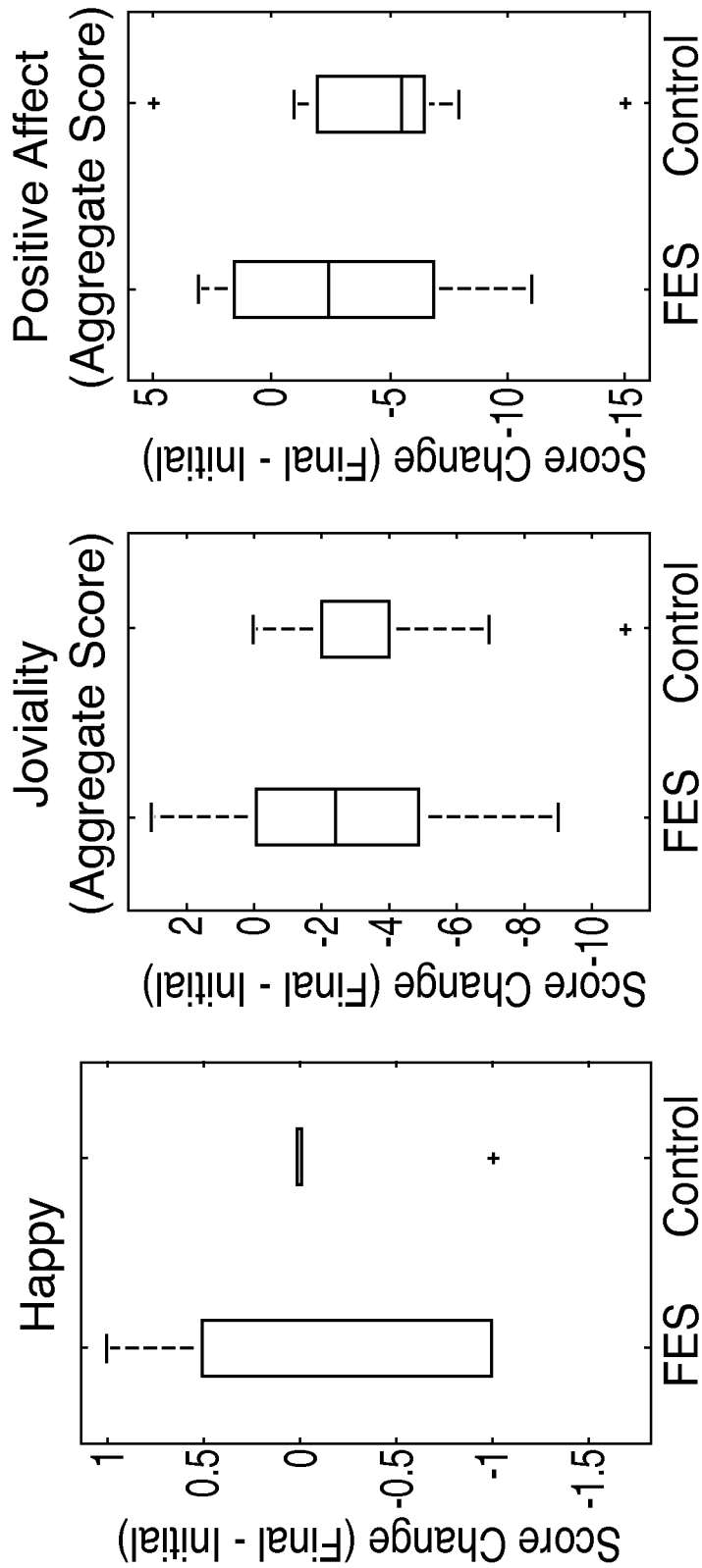
FIG. 3 shows boxplots comparing the change score distributions for the FES and control groups on three mood parameters.

The primary outcomes, constituting a generalized mood descriptions of "happy", "joviality", and "positive affect" did not show any significant differences between the two groups, although some qualitative differences are visible in the exemplary boxplots of FIG. 3. In particular there is a wider range of effects on the "happy" item in the FES group than in the control group. On the other hand, the secondary outcomes that showed a significant difference are highly relevant to MDD, for example. The increase in "determination" in particular, and to a lesser extent the increase in "daring" and decrease in "scared", contrast strongly with the feelings of helplessness and lethargy that can accompany MDD. A reduced ability to concentrate is also a symptom of depression, so an increase in the "concentrating" item would have been desirable rather than the observed decrease, but as stated above it is likely that this effect was due to the FES sensation rather than a neuromodulatory effect.

The effects of the FES may have been partly obscured by the experimental procedures (cognitive task), which themselves had a negative impact on the primary outcomes (FIG. 4). Nonetheless, these procedures were judged to be necessary to present a plausible deception that would justify the use of facial FES in able-bodied individuals and minimize the likelihood of the participants guessing the true purpose of the study. The FES stimulation itself can also arguably be unpleasant, and the sensation of the FES may therefore have counteracted any positive neuromodulatory impact on positive affect. When asked to report the pleasantness or unpleasantness of the FES, however, participant responses were neutral, suggesting that this potential confounding factor was not a major issue. In addition, during the assessments the Water-Level Task was always administered first, ensuring that a few minutes had elapsed between the end of the FES sensation and the final PANAS-X thereby allowing the individuals to somewhat "forget" the sensation before rating their affect.

Another consequence of the need for a deception was that the cognitive task reduced the ability of the individuals to focus entirely on their facial movements while receiving the FES. This was mitigated to an extent by the inclusion of Task 1, which involved only receiving FES and performing the voluntary movements, without the addition of the cognitive task. Nonetheless, this task represented half of the FES time and thus only a quarter of the total experiment time (12.5 minutes), whereas the other half of the FES time included the distraction of the cognitive task. The voluntary component was thought to enhance the effectiveness of FES therapy, and therefore it is possible that the stimulation periods in which there was a distraction may have been less effective. Higher doses of FES therapy with no distractions may yield stronger effects. On the other hand, the fact that several significant results were obtained even with the limited dose of FES argues in favour of the viability of the method.

The above experiment investigated whether FES enhances the mood-related effects of voluntarily activating facial muscles with close neural connections to the subcortical nuclei regulating emotions. Although the primary outcomes in the FES group were not significantly different from those in the control group, several secondary outcomes with potential relevance to MDD did show significant differences. Therefore, facial FES to produce facial expressions associated with various moods may be used to elicit various moods in individuals. Thus FES may indeed be used to modulate mood, even with small doses.

The foregoing terms as well as other terms should be broadly interpreted throughout this application to include all known as well as all hereafter discovered versions, equivalents, variations and other forms of the abovementioned terms as well as other terms.

Any embodiment of the present invention may include any of the optional or exemplary features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention.

It is to be understood that the above description is intended to be illustrative, and not restrictive. The disclosure is intended to cover various modifications, uses, adaptations, and equivalent arrangements based on the principles disclosed. Further, this application is intended to cover such departures from the present disclosure as come within at least the known or customary practice within the art to which it pertains. Many other embodiments will be apparent to those skilled in the art, upon reviewing the above description. The scope of the invention should, therefore, be determined with reference to the appended claims, along with the full scope of equivalents to which such claims are entitled.

Although the present invention has been described with reference to specific example embodiments, it will be evident that various modifications and changes may be made to these embodiments without departing from the broader spirit and scope of the disclosed subject matter.

The invention claimed is:

1. A method for treating a subject afflicted with a depressive disorder associated with a mood or an emotional state, comprising: applying functional electrical stimulation to at least one facial muscle associated with said mood or emotional state to activate one or more neural tracts of at least one of the extrapyramidal or pyramidal motor systems of said subject, thereby improving a mood parameter or emotional state of the subject, thereby to treat the subject, wherein the functional electrical stimulation further comprises:
   a) placing electrode pairs on the face of the subject to establish an electric circuit along at least one orbicularis oculi muscle and along at least one zygomatic major muscle using a plurality of biphasic pulses, wherein each biphasic pulse is delivered for a duration of from about 25 μsec to about 1000 μsec;
b) delivering said biphasic pulses to stimulate said at least one orbicularis oculi muscle;
c) delivering said biphasic pulses to stimulate said at least one zygomatic major muscle;
d) discontinuing said biphasic pulses to allow said muscles to relax; and
e) repeating steps b), c) and d) at least once.

2. The method according to claim 1, wherein said functional electrical stimulation triggers a Duchenne marker.

3. The method according to claim 1, wherein said functional electrical stimulation is applied to two orbicularis oculi muscles through a corresponding number of electrode pairs.

4. The method according to claim 1, wherein each one of said biphasic pulses is delivered with an amplitude of from about 1 mA to about 15 mA.

5. The method according to claim 4, wherein each one of said biphasic pulses is delivered with an amplitude of from about 1 mA to about 10 mA.

6. The method according to claim 1, wherein said plurality of biphasic pulses are delivered at from about 16 Hz to about 100 Hz.

7. The method according to claim 6, wherein said plurality of biphasic pulses are delivered at from about 20 Hz to about 60 Hz.

8. The method according to claim 1, wherein said plurality of biphasic pulses is delivered for a time period of at least 1 second.

9. The method according to claim 1, wherein each one of said biphasic pulse is delivered for a duration of about 150 μsec to about 400 μsec.

10. The method according to claim 1, wherein steps (b) to (d) are repeated at least 5 times over the course of about one hour.

11. The method according to claim 1, wherein steps (b) to (d) are repeated about 25 times over the course of about one hour.

12. The method according to claim 1, comprising stimulating both orbicularis oculi muscles bilaterally located on said face of said subject.

13. The method according to claim 1, comprising stimulating both zygomatic major muscles bilaterally located on said face of said subject.

14. The method according to claim 1, wherein said functional electrical stimulation modulates subcortical nuclei activity through at least one of the extrapyramidal motor system or cortical brain region activity through the pyramidal motor system related to an associated given emotion.

15. The method according to claim 1, wherein for a subject afflicted with major depressive disorder, and said method improves a mood parameter or emotional state of the subject.

16. The method according to claim 1, further comprising, in advance of the applying electrical stimulation, detecting a voluntary smile by the subject.

17. The method according to claim 16, wherein the detecting a voluntary smile includes measuring electromyography of a first set of one or more selected face muscles, and directing the applying step at the first and/or a second set of one or more selected face muscles.

18. The method of claim 1, wherein the at least one facial muscle is substantially undamaged or unblocked.

19. A method for treating a subject afflicted with a depressive disorder associated with a mood or an emotional state, comprising:
a. placing at least one first pair of electrodes bilaterally on the face of the subject to establish an electric circuit along at least one substantially undamaged orbicularis oculi muscle and placing at least one second pair of electrodes bilaterally on the face of the subject to establish an electric circuit along at least one substantially undamaged zygomatic major muscle, for delivering a plurality of biphasic pulses, with each having a duration of from about 25 μsec to about 1000 μsec;
b. delivering said biphasic pulses to stimulate said at least one orbicularis oculi muscle and said at least one zygomatic major muscle so as to trigger a Duchenne marker and produce a smile by the subject;
c. discontinuing said biphasic pulses to allow said muscles to relax; and,
d. repeating steps b and c at least once.

* * * * *